United States Patent [19]

Miura et al.

[11] Patent Number: 5,399,758
[45] Date of Patent: Mar. 21, 1995

[54] DIACYLHYDRAZINE PHOTO-REACTIVE COMPOUNDS

[75] Inventors: Toshimasa Miura, Fujisawa; Ryoichi Sudo, Yokosuka; Saori Matsuda; Fumio Kataoka, both of Yokohama, all of Japan

[73] Assignee: Hitachi, Ltd.,, Tokyo, Japan

[21] Appl. No.: 979,225

[22] Filed: Nov. 20, 1992

[30] Foreign Application Priority Data

Nov. 20, 1991 [JP] Japan ................... 3-304815

[51] Int. Cl.⁶ .......................................... C07C 243/28
[52] U.S. Cl. ..................... 564/150; 564/148; 564/149; 564/151
[58] Field of Search ................ 564/148, 149, 150, 151

[56] References Cited

U.S. PATENT DOCUMENTS 2,990,417  6/1961  Carboni ..................... 564/151 X
5,225,443  7/1993  Murphy et al. ............. 564/149 X

*Primary Examiner*—Richard L. Raymond
*Attorney, Agent, or Firm*—Antonelli, Terry, Stout & Kraus

[57] ABSTRACT

Disclosed are a novel azide compound represented, for example, by the formula,

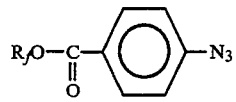

wherein $R_f$ represents a fluoroalkyl or fluoroalkylpolyether group,

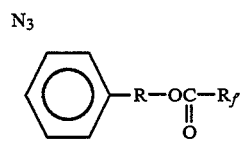

wherein R represents a divalent organic group having an ester bond, and $R_f'$ represents a fluoroalkylpolyether group, and a novel diacylhydrazine compound having a fluoroalkylpolyether group in the side chain and lubricants containing them. When this lubricant is coated onto the carbonaceous protective film of magnetic recording media and reacted by the action of light or heat, it strongly bonds or adheres to the protective film. Thus, the durability of the lubricant improves, as a result of which a high-density magnetic recording medium having a high reliability and long life can be obtained.

7 Claims, 3 Drawing Sheets

DIACYLHYDRAZINE PHOTO-REACTIVE COMPOUNDS

BACKGROUND OF THE INVENTION

FIELD OF THE INVENTION

The present invention relates to novel azide and diacylhydrazine compounds, lubricants with them formed in the form of lubricating film on a sliding surface, particularly functional lubricants suitable to apply to the sliding surface for magnetic head of high-density magnetic recording media, a method and apparatus for applying the above lubricants and magnetic recording media with the film of the lubricants.

DESCRIPTION OF THE PRIOR ART

Hitherto, various lubricants used for magnetic recording media, particularly magnetic disks have been studied, and among them, fluorine-containing polyether derivatives are known to be effective. Studies on the derivatives are disclosed, for example, in Japanese Patent Application Kokai No. 64-59614, No. 1-131132 and No. 1-268664.

Recently, with an increase in the density of magnetic records on magnetic disks, the hardness of a protective film for the disks becomes high, with which the thickness of the protective film becomes small. There are many protective films of this sort, among which carbonaceous ones are regarded as promising. However, conventionally used lubricants are poor in adhesion to these carbonaceous protective films, and also a tendency for the durability of the lubricants to become low is observed.

Techniques so far employed for solving these problems are disclosed in Japanese Patent Application Kokai No. 62-65226 and No. 62-109229. However, magnetic disks which have been regarded as the target of these techniques are a coating disk produced by coating the substrate for magnetic disks with the dispersion liquid of a magnetic substance in an epoxy resin, this coating disk being subsequently treated with an azide compound at the surface and then coated with a perfluoroalkylpolyether as a lubricant. However, the process of these techniques is complicated, having difficulties in putting it to practical use.

On the other hand, the target of the present invention is a sputtered disk obtained by sputtering, for example, a Co-Cr magnetic substance onto the substrate. This process is advantageous in terms of practical use because the novel azide or diacylhydrazine compound itself, used as a surface-treating agent, acts as the lubricant, as a result of which only one coating step will suffice.

Also, a method of irradiating the disk with deep UV light after coating the lubricant is known. This method, however, has a problem that the thickness of the lubricant film is too small, so that the durability is inferior. Studies on this method are disclosed, for example, in Langmuir (a journal of American Chemical Society), 1990, 6, 1522–1524.

SUMMARY OF THE INVENTION

An object of the present invention is to solve the above conventional problems, thereby providing novel azide and diacylhydrazine compounds which function as a surface-treating agent, i.e. a lubricant, having a high adhesion property and excellent durability, and a lubricant containing the above compounds.

Another object of the present invention is to provide a method for coating the above lubricant onto a material to be treated.

A further object of the present invention is to provide an apparatus for coating the above lubricant.

A still further object of the present invention is to provide a magnetic recording medium surface-treated with the above lubricant.

Other objects and advantages of the present invention will become apparent from the following description.

DESCRIPTION OF THE PREFERRED EMBODIMENTS

Figure 1:
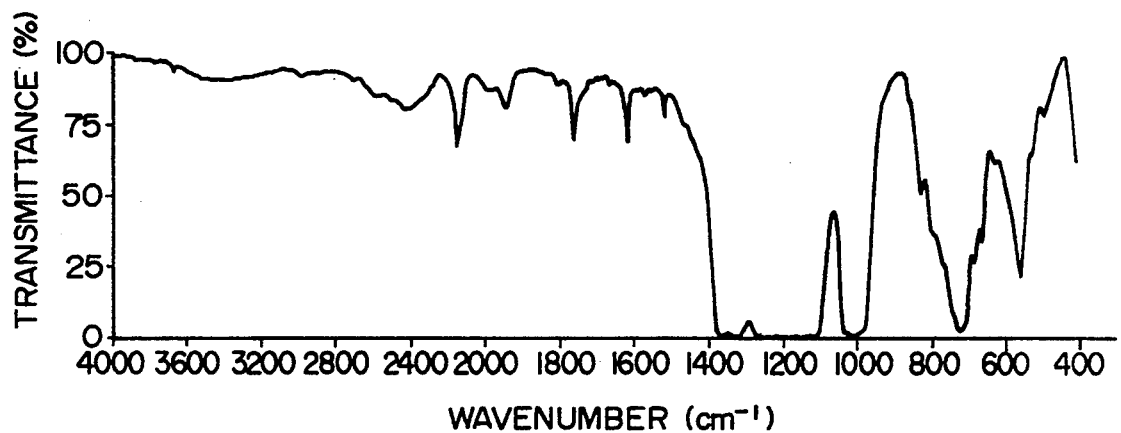
FIG. 1 shows the IR spectrum of the azide compound of the present invention.

The novel azide compound of the present invention is used as the main component of the lubricant, and as specifically shown below, it is a novel reactive azide compound having a fluoroalkyl or fluoroalkylpolyether group in the side chain and reacting by the action of light or heat. This compound is shown in the following five groups.

1st group:

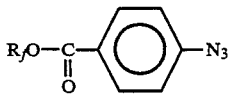
(1)

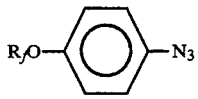
(2)

(3)

$R_fN_3$ (4)

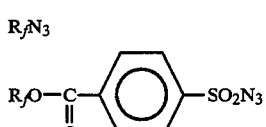
(5)

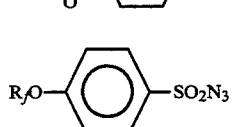
(6)

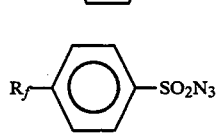
(7)

$R_fSO_2N_3$ (8)

wherein $R_f$ in the formulae 1 to 3 and 5 to 8 represents a fluorocarbon-containing side chain represented by $R_{f1}$, or a fluoroalkylpolyether group represented by either one of $R_{f2}$ and $R_{f3}$ (in which n is 4 to 1,500) and $R_f$ in the formula 4 represents a fluoroalkylpolyether group represented by either one of $R_{f2}$ and $R_{f3}$ (in which n is 4 to 1,500), P is 6 or more and q is a positive integer,

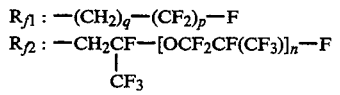
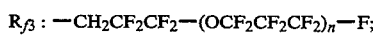

2nd group:

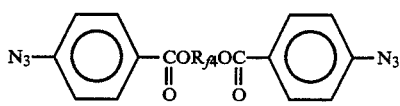  (9)

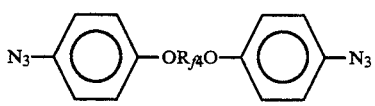  (10)

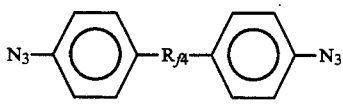  (11)

$N_3R_{f4}N_3$  (12)

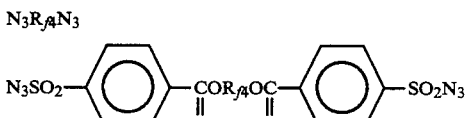  (13)

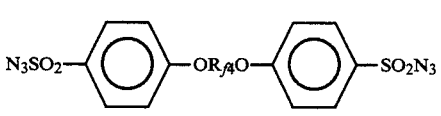  (14)

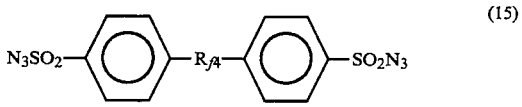  (15)

$N_3SO_2R_{f4}SO_2N_3$  (16)

wherein $R_{f4}$ in the formulae 9 to 16 represents a fluoroalkylpolyether group represented by the following formula in which each of l and m is 2 to 750,

3rd group:

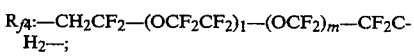  (17)

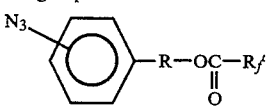  (18)

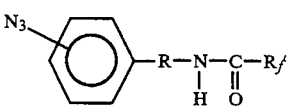  (19)

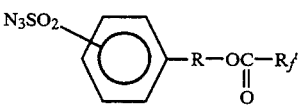  (20)

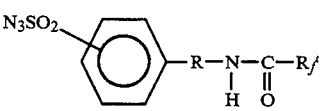

wherein in the formulae 17 to 20, R represents a divalent organic group having an ester bond, and $R_f'$ represents a fluoroalkylpolyether group; and preferably, R represents a divalent organic group having an ester bond represented by either one of $R_1$, $R_2$, $R_3$ and $R_4$ and $R_f'$ represents a fluoroalkylpolyether group represented by either one of $R_{f1}'$ and $R_{f2}'$ in which n is 4 to 1,500, $R_1$ : $-COOCH_2CH_2-$,
$R_2$ : $-CH=CHCOOCH_2CH_2-$,
$R_3$ : $-CH=C(CN)COOCH_2CH_2-$,
$R_4$ : $-CH=CHCOOC_6H_4CH_2CH_2-$

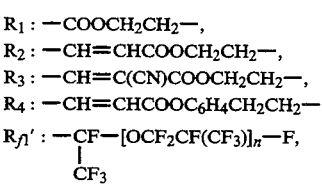
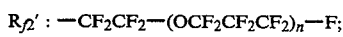

4th group:

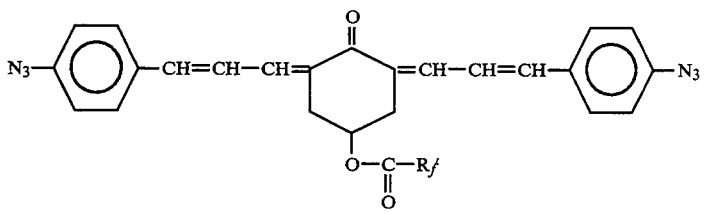  (21)

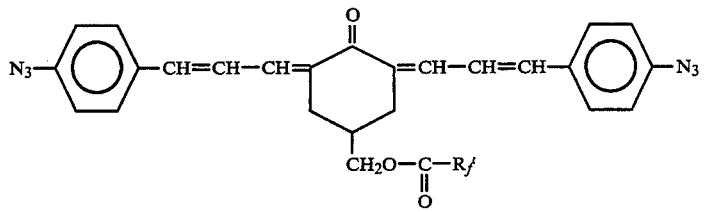 (22)

wherein $R_f'$ in the formulae 21 and 22 represents a fluoroalkylpolyether group represented by either one of $R_{f1}'$ in which n is 4 to 1,500,

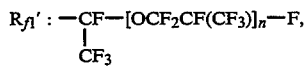

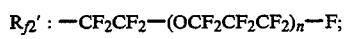

5th group:

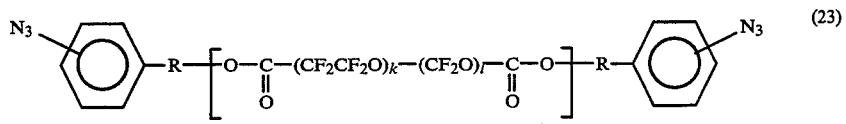 (23)

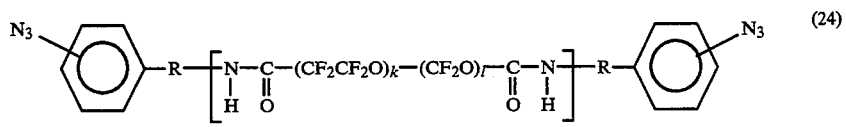 (24)

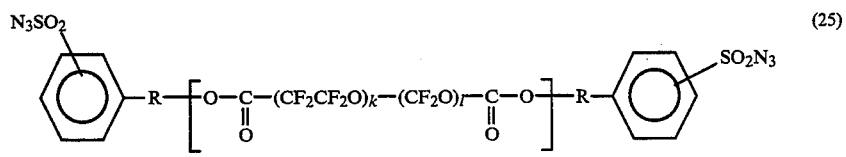 (25)

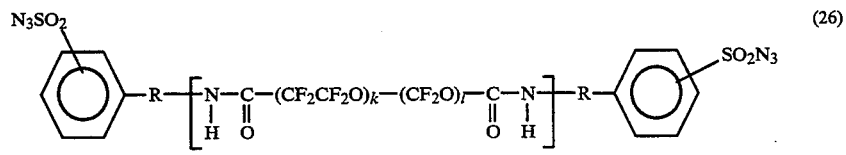 (26)

wherein in the formulae 23 to 26, R represents a divalent organic group having an ester bond represented by either one of $R_1$, $R_2$, $R_3$ and $R_4$, k is 4 to 1,500 and l is 4 to 1,500, $R_1$: —COOCH$_2$CH$_2$—,
$R_2$: —CH=CHCOOCH$_2$CH$_2$—,
$R_3$: —CH=C(CN)COOCH$_2$CH$_2$—,
$R_4$: —CH=CHCOOC$_6$H$_4$CH$_2$CH$_2$—.

The novel diacylhydrazine compound of the present invention also is used as the main component of the lubricant, and as specifically shown below, it is a novel diacylhydrazine compound having a fluoroalkylpolyether group in the side chain,

 (27)

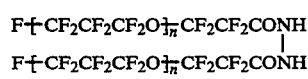 (28)

F$\pm$CF$_2$CF$_2$CF$_2$O$\pm_n$CF$_2$CF$_2$CONHNHCOR (29)

$F-\left[\begin{array}{c}CFCF_2O\\|\\CF_3\end{array}\right]_n-CFCONHNHCOR$ (30)
$\qquad\qquad\qquad\qquad CF_3$ F$\pm$CF$_2$CF$_2$CF$_2\pm_n$CF$_2$CF$_2$CONHNHCOCF$-\left[\begin{array}{c}OCF_2CF\\|\\CF_3\end{array}\right]_n-$F (31)
$\qquad\qquad\qquad\qquad\qquad\qquad\qquad\qquad CF_3$ (OC—(CF$_2$CF$_2$O)$_k$—(CF$_2$O)$_l$CO—NHNH)$_n$ (32)

F$\pm$CF$_2$CF$_2$CF$_2$O$\pm_n$CF$_2$CF$_2$COOH (33)

$F-\left[\begin{array}{c}CFCF_2O\\|\\CF_3\end{array}\right]_n-CFCOOH$ (34)
$\qquad\qquad\qquad CF_3$ wherein k is 1 to 5, l is 1 to 10 and n is 1 to 10.

The molecular weight of the above reactive azide and diacylhydrazine compounds is preferably 500 to 200,000. In order that the compounds may exhibit a sufficient lubricating action, the molecular weight is preferably 2,000 to 10,000. When the molecular weight is less than 500, the surface-treating agent becomes easy to scatter during the coating operation, and the lubricating action also tends to lower. When the molecular weight is larger than 500,000, the relative concentration of the azide compound lowers to make development of the adhesion property difficult.

The lubricant of the present invention contains components for the conventional lubricants in addition to the above main components.

A coating method for the lubricant of the present invention comprises a step in which the above reactive lubricant is dissolved in a fluorine-containing solvent and a material to be treated is immersed in the resulting solution and then pulled up therefrom to form the film of the lubricant on its surface, and a step in which, during or after formation of the above film, the film is heated or irradiated with an energy beam to allow the lubricant constituting it to cause a denitrogenation reaction.

The concentration of the lubricant is 0.001 to 1 wt. %, preferably 0.01 to 0.1 wt. %, it being preferred to adjust the concentration according to the required thickness of the film.

In order to allow the above reactive azide compound to cause the denitrogenation reaction, it is desired to allow the reaction to occur in a non-oxidizing atmosphere (e.g. nitrogen) so as not to cause oxidation of the lubricant. The material to be treated to which the lubricant of the present invention can be applied includes, for example, adhesive tapes, various masks used in lithography, molds for molding plastics and the like, including magnetic recording media (including disks and tapes). The lubricant of the present invention is effective to surface treatment of any material requiring a lubricating film.

The lubricant of the present invention can be applied not only by the above coating method, but also by a method using an apparatus shown in FIG. 2 as described later in detail in the examples, Langmuir-Blodgett (LB) method, dipping method, rotational coating with a spinner, and the like. These methods can properly be selected. The thickness of film of the lubricant can be regulated by coating conditions, solution concentrations and treatment conditions after coating.

A coating apparatus for the lubricant of the present invention comprises a lubricant-storing vessel, a reaction vessel connected to the opening of the above storing vessel, a conveying means which introduces a material to be treated from the outside into the storing vessel, immerses the material in the lubricant and after immersing, pull-up the material while moving the material at a pre-determined speed in the reaction vessel, a gas-introducing means for keeping the inner part of the reaction vessel in a non-oxidizing gas atmosphere and a means fixed to the periphery of the reaction vessel which allows the lubricant coated onto the surface of the material to cause the denitrogenation reaction while the material passes through the reaction vessel, thereby strongly adhering the lubricant to the material.

The non-oxidizing gas may be any of those which do not oxidize the lubricant and, for example, a nitrogen gas is practically preferred.

As a means to strongly adhere the lubricant to the carbonaceous protective film by the denitrogenation reaction of the reactive azide compound or reaction of the diacylhydrazine compound, energy beams having a wavelength of 20 to 400 nm (e.g. ultraviolet ray) are preferred, and a high-pressure mercury lamp is practical. Also, heating means such as heaters are effective. The heating temperature is 80° to 250° C., preferably 100° to 200° C. It is desirable to heat the lubricant for 5 to 60 minutes at a temperature selected from this range.

The magnetic recording medium of the present invention includes an improvement wherein the film of the above lubricant is formed on the protective film. Those which are effective as this protective film include known metal oxides, nitrides and carbonaceous substances, and the like. Particularly, the lubricant of the present invention has a good affinity to the carbonaceous protective film, so that a lubricating film which has strongly and stably bonded to the protective film can be realized.

In one embodiment of the present invention, in order to improve adhesion of the lubricant to the material to be treated, thereby giving excellent durability to the lubricant, an azide group, a photoreactive functional group, was introduced into a fluoroalkylpolyether compound. This compound, as described above, is also reactive to heat. And after reaction, this compound acquires excellent properties that it forms a strong bond with the material to be treated, is rich in adhesion property and has a heat resistance sufficiently resisting 300° C. Consequently, when this compound is used as the lubricating film of various sliding surfaces, release agent of adhesive tapes and release film formed on the surface of a mold at the time of molding of plastics, it acts as a long-life lubricating film in any case.

Explanation will be given on a case where the material to be treated is a magnetic disk having a carbonaceous film formed on the surface. The lubricant of the present invention was dissolved in a solvent and coated onto the magnetic disk, after which the coating film on the magnetic disk was irradiated with ultraviolet ray using a 500 W high-pressure mercury lamp in a nitrogen gas atmosphere. Thus, a strong bond is obtained, the reason for this being thought as follows.

The azide compound in the coating film releases nitrogen to generate nitrene (nitrogen homologue of carbene, R-N:) which is a reactive intermediate. This reaction, is called a denitrogenation reaction. The nitrene reacts in the form of radical with the surface of the carbonaceous protective film to form a strong bond and further form a network between the lubricants. Also, a certain degree of effect could be obtained by heating in place of irradiation with ultraviolet ray.

In another embodiment of the present invention, in order to improve adhesion of the lubricant to the protective film of the magnetic recording medium, thereby giving excellent durability to the lubricant, a hydrazide group, a reactive functional group, was introduced into a fluoroalkylpolyether compound. This lubricant was dissolved in a solvent and coated onto the magnetic recording medium which was then irradiated with ultraviolet ray using a 500 W high-pressure mercury lamp. It is considered that by this treatment, the surface of the protective film and hydrazide portion react with each other to form a strong bond. Similarly, the same effect was obtained by heating the magnetic recording medium coated with the lubricating substance.

The lubricant of the present invention is used in solution in a suitable organic solvent taking ease of coating, thickness of the coating film and the like into account. The solvent used in this case is preferably a fluorine-containing solvent in terms of solubility. It is not however limited thereto, and any of solvents which dissolve this sort of lubricant may be used.

The magnetic recording medium, a target to be coated with the lubricant of the present invention, includes magnetic disks covered with the carbonaceous protective film. The magnetic disks are constituted as shown in FIG. 2. That is, the magnetic disks have a structure that a ground layer (2) such as Ni-P and a magnetic film (3) are vacuum-deposited in this order onto a substrate (1) such as Al, and further a carbonaceous protective film (4) is applied thereto by the sputtering method or plasma CVD method. In the sputtering method, the carbonaceous protective film is formed as follows: A magnetic disk is placed in a vacuum of $10^{-6}$ Torr or more, an argon gas (gas pressure, 10 mTorr) is introduced into the vacuum and sputtering is carried out with graphite as target. The plasma CVD method (chemical vaporing deposition) refers to a method of forming a thin film by the reaction on substrate of ions or radicals produced by electrolytic dissociation or plasma reaction of a gas used as material. The protective film formed by this method has a property that it has high hardness, transparency and resistance and is chemically inactive.

In addition to the above magnetic disk, magnetic tapes and the like also are included in the target to be coated with the lubricant of the present invention. The lubricant of the present invention can be applied to other various apparatus without being limited to magnetic recording media. As described above, by coating the lubricant having the introduced hydrazide and subjecting the lubricant to irradiation with ultraviolet ray or heat-treatment, the lubricant could be strongly adhered to the carbonaceous protective film on magnetic recording media, and thus the reliability and durability of magnetic recording media could be improved.

In addition to the above magnetic disks, magnetic tapes and the like also are included in the material to be treated onto which the lubricant of the present invention is coated. As described above, the lubricant of the present invention can be applied out only to the magnetic recording media, but also to other materials such as for example adhesive tapes, various masks used in lithography, molds for molding plastics, and the like, being effective to the surface-treatment of any material requiring a lubricating film. Particularly, when the surface of the material to be treated is composed of a carbonaceous material, by applying a lubricating film to the carbonaceous protective film on magnetic recording media and allowing the lubricating film to cause the denitrogenation reaction as described above, the lubricating film can strongly be adhered to the protective film, and thus magnetic recording media having improved reliability and durability can be realized.

The present invention will be illustrated in more detail with reference to the following examples, which are not however to be interpreted as limiting the invention thereto.

EXAMPLES 1 to 33

(1) Synthesis of azide compounds

Fluoroalkylalcohol represented by the formula 35 and fluoroalkylpolyetheralcohols represented by the formulae 36 and 37,

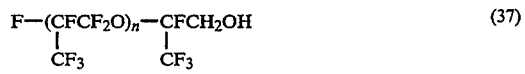

wherein p is 6, q is 1 and n is 20 to 30, were separately reacted with p-azidobenzoic acid chloride represented by the formula 38,

in the presence of a base to obtain azide compounds represented by the formulae 39, 40 and 41, respectively, in a high yield,

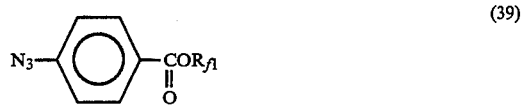

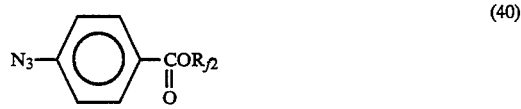

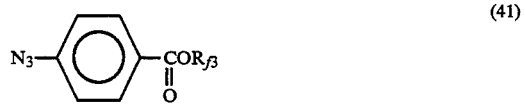

wherein $R_{f1}$, $R_{f2}$ and $R_{f3}$ are as shown below,

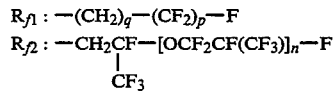

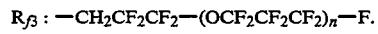

Similarly, the same fluoroalkylalcohol (35) and fluoroalkylpolyetheralcohols (36) and (37) as described above were separately reacted with an acid chloride represented by the formula 42,

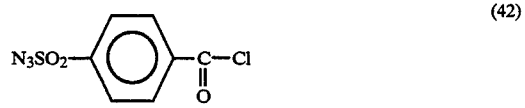

in the presence of a base to obtain azide compounds represented by the formulae 43, 44 and 45, respectively, in a high yield,

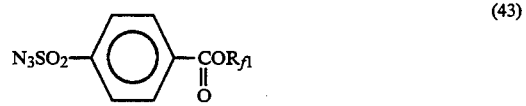

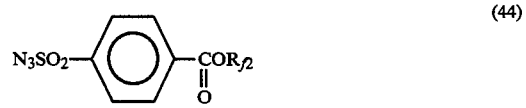

-continued

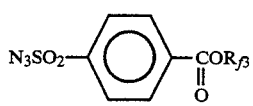

wherein $R_{f1}$, $R_{f2}$ and $R_{f3}$ are as shown below,

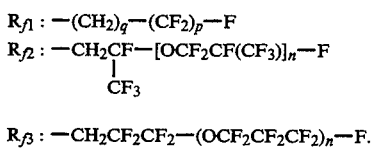

Fluoroalkylalcohol of the formula 35 (wherein p is 6 and q is 1) and fluoroalkylpolyetheralcohols of the formulae 36 and 37 (wherein n is 20 to 30) were separately converted to the corresponding bromides with phosphorus tribromide. The resulting bromides were separately reacted with each of the compounds represented by the formulae 46 and 47,

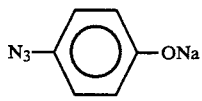 (46)

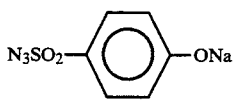 (47)

to obtain azide compounds represented by the formulae 48, 49, 50, 51, 52 and 53, respectively, in a high yield,

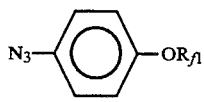 (48)

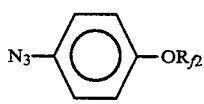 (49)

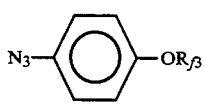 (50)

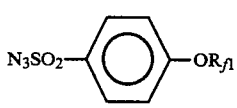 (51)

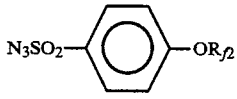 (52)

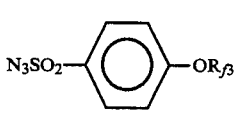 (53)

wherein $R_{f1}$, $R_{f2}$ and $R_{f3}$ are as shown below.

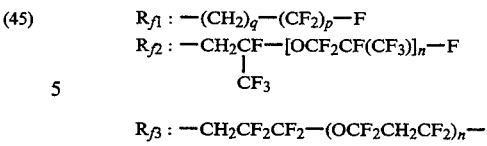

Similarly, fluoroalkylalcohol of the formula 35 (wherein p is 6 and q is 1) and fluoroalkylpolyetheralcohols of the formulae 36 and 37 (wherein n is to 30) were separately converted to the corresponding bromides with phosphorus tribromide. The resulting bromides were separately reacted with each of the compounds represented by the formulae 54 and 55,

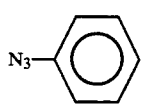 (54)

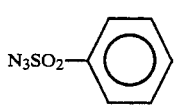 (55)

in the presence of aluminum chloride to obtain azide compounds represented by the formulae 56, 57, 58, 59, 60 and 61, respectively, in a high yield,

 (56)

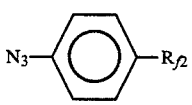 (57)

 (58)

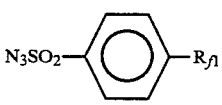 (59)

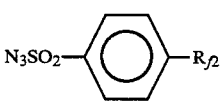 (60)

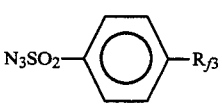 (61)

wherein $R_{f1}$, $R_{f2}$ and $R_{f3}$ are as shown below,

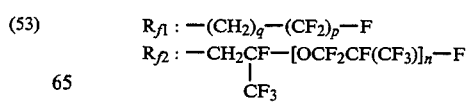

Further, fluoroalkylalcohol of the formula 35 (wherein p is 6 and q is 1) and fluoroalkylpolyetheralcohols of the formulae 36 and 37 (wherein n is 20 to 30) were separately converted to the corresponding bromides with phosphorus tribromide. The resulting bromides were separately reacted with sodium azide to obtain surface-treating agents (62), (63) and (64), respectively, $$R_{f1}N_3 \quad (62)$$

$$R_{f2}N_3 \quad (63)$$

$$R_{f3}N_3 \quad (64)$$

wherein $R_{f1}$, $R_{f2}$ and $R_{f3}$ are as shown below, $R_{f1}$ : $-(CH_2)_q-(CF_2)_p-F$ $R_{f2}$ : $-CH_2CF-[OCF_2CF(CF_3)]_n-F$
            $\quad\quad\, |$
            $\quad\,\, CF_3$ $R_{f3}$ : $-CH_2CF_2CF_2-(OCF_2CH_2CF_2)_n-F$.

Similarly, fluoroalkylalcohol of the formula 35 (wherein p is 6 and q is 1) and fluoroalkylpolyetheralcohols of the formulae 36 and 37 (wherein n is 20 to 30) were separately converted to the corresponding sulfonic acid chlorides. The resulting sulfonic acid chlorides were separately reacted with sodium azide to obtain surface-treating agents (65), (66) and (67), respectively, $$R_{f1}SO_2N_3 \quad (65)$$

$$R_{f2}SO_2N_3 \quad (66)$$

$$R_{f3}SO_2N_3 \quad (67)$$

wherein $R_{f1}$, $R_{f2}$ and $R_{f3}$ are as shown below, $R_{f1}$ : $-(CH_2)_q-(CF_2)_p-F$ $R_{f2}$ : $-CH_2CF-[OCF_2CF(CF_3)]_n-F$
            $\quad\quad\, |$
            $\quad\,\, CF_3$ $R_{f3}$ : $-CH_2CF_2CF_2-(OCF_2CH_2CF_2)_n-F$.

Fluoroalkylpolyetheralcohol represented by the formula 68, $$HOR_{f4}OH \quad (68)$$

wherein $R_{f4}$ is $-CH_2CF_2-(OCF_2CF_2)_l-(OCF_2)_m-CF_2CH_2-$ (in which l is 3 to 7 and m is 7 to 13), was reacted with each of the foregoing acid chlorides (38) and (42) to obtain surface-treating agents represented by the formulae 9 and 13, respectively. The compound (68) was reacted with each of the compounds (46) and (47) to obtain azide compounds represented by the formulae 10 to 14, respectively. The compound (68) was converted to the corresponding bromide with phosphorus tribromide, and the bromide was reacted with each of the compounds (54) and (55) in the presence of aluminum chloride to obtain azide compounds represented by the formulae 11 and 15, respectively. The above bromide was reacted with sodium azide to obtain an azide compound represented by the formula 12. Further, the compound (68) was converted to the corresponding sulfonic acid chloride which was then reacted with sodium azide to obtain an azide compound represented by the formula 16.

Lubricants containing as a main component the azide compounds thus obtained were prepared.

(2) Formation of lubricating film and evaluation of its characteristics

① Preparation of material to be treated

Figure 2:
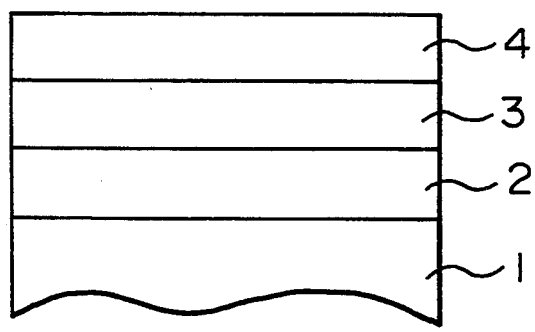
FIG. 2 shows the structural view of the magnetic disk of the present invention.

The material to be treated used here to coat the surface-treating agent of the present invention is a magnetic recording medium having a sectional structure shown in FIG. 2. This magnetic recording medium is composed of a magnetic disk of which the surface has previously been covered with a carbonaceous protective film. Referring to the constitution of the magnetic disk according to the drawing, the magnetic disk has a structure that a ground layer (2) such as Ni-P and a magnetic film (3) are vacuum-deposited in this order onto a non-magnetic substrate (1) such as Al, and further a carbonaceous protective film (4) is applied thereto by the sputtering method or plasma CVD method. In the sputtering method, the carbonaceous protective film is formed as follows: A magnetic disk is placed in a vacuum of $10^{-6}$ Torr or more, an argon gas (gas pressure, 10 mTorr) is introduced into the vacuum and sputtering is carried out with graphite as target. The plasma CVD method (chemical vaporing deposition) refers to a method of forming a thin film by the reaction on substrate of ions or radicals produced by electrolytic dissociation or plasma reaction of a gas used as material. The protective film formed by this method has a property that it has high hardness, transparency and resistance and is chemically inactive.

② Formation of lubricating film on material to be treated

Three grams of each of the compounds (9) to (16), (39) to (41), (43) to (45), (48) to (53) and (56) to (67) synthesized by the above methods was dissolved in 27 g of a fluorine-containing solvent having a boiling point of 100° C. to prepare a 1 wt. % solution. These solutions were used as a surface-treating solution. The solvent used was a perfluorocarbon oil, Fluorinert (trade name of Sumitomo 3M Co.).

Magnetic disks, 5 inches in diameter, covered with an amorphous carbonaceous protective film of 20 nm in film thickness previously formed by the CVD method, were prepared for. Every magnetic disk was immersed in the above surface-treating solutions for 10 minutes, pulled up at a rate of 0.5 cm/min and dried. Thereafter, the magnetic disk was irradiated for 3 minutes with 25 mW ultraviolet ray having a wavelength of 365 nm from a 500 W high-pressure mercury lamp in a nitrogen atmosphere. Thus, formation of a lubricating film on the carbonaceous protective film was finished. Thereafter, for the purpose of the subsequent evaluation test, the disk was immersed in a fluorine-containing solvent having a boiling point of 100° C. and rinsed by ultrasonic wave irradiation.

③ Evaluation of characteristics

The intensity of C-F stretching vibration of the lubricating film was measured with a Fourier transformation infrared spectrophotometer (abbreviated as FT-IR), and the intensity of C-F stretching vibration before and after rinsing by ultrasonic wave irradiation was compared to obtain a lubricating film retention. The contact.start.stop (CSS) test was carried out on the magnetic disk having a lubricating film formed thereon at a peripheral speed of 20 m/sec with a load of 20 g applied thereto by point contact, and a frictional force after the CSS test was measured. These results are shown in Examples 2 to 33 of Table 1.

In Table 1, a lubricating film retention of 80% or more was indicated by ○, and that of less than 80% was indicated by x. The frictional force after the CSS test was obtained as static friction coefficient, and the coefficients of less than 0.13, 0.13 to 0.20 and more than 0.20 were indicated by ⊙, ○ and x, respectively.

TABLE 1

| Example | Compound | Durability test for lubricating film | |
|---|---|---|---|
| | | Ultrasonic wave rinsing | CSS test (10000 times) |
| 2 | (9) | ○ | ⊙ |
| 3 | (10) | ○ | ⊙ |
| 4 | (11) | ○ | ⊙ |
| 5 | (12) | ○ | ○ |
| 6 | (13) | ○ | ⊙ |
| 7 | (14) | ○ | ⊙ |
| 8 | (15) | ○ | ⊙ |
| 9 | (16) | ○ | ○ |
| 10 | (39) | ○ | ○ |
| 11 | (40) | ○ | ⊙ |
| 12 | (41) | ○ | ○ |
| 13 | (43) | ○ | ⊙ |
| 14 | (44) | ○ | ⊙ |
| 15 | (45) | ○ | ⊙ |
| 16 | (48) | ○ | ○ |
| 17 | (49) | ○ | ⊙ |
| 18 | (50) | ○ | ⊙ |
| 19 | (51) | ○ | ○ |
| 20 | (52) | ○ | ⊙ |
| 21 | (53) | ○ | ⊙ |
| 22 | (56) | ○ | ○ |
| 23 | (57) | ○ | ⊙ |
| 24 | (58) | ○ | ⊙ |
| 25 | (59) | ○ | ○ |
| 26 | (60) | ○ | ⊙ |
| 27 | (61) | ○ | ⊙ |
| 28 (Reference) | (62) | ○ | ○ |
| 29 | (63) | ○ | ○ |
| 30 | (64) | ○ | ○ |
| 31 | (65) | ○ | ○ |
| 32 | (66) | ○ | ○ |
| 33 | (67) | ○ | ○ |

In Examples described above, magnetic disks covered with the amorphous carbonaceous protective film formed by the CVD method were used as the material to be treated. In the following Examples 34 to 65, magnetic disks covered with the carbonaceous protective film formed by sputtering method were used.

Examples 34 to 65

In the same manner as in the foregoing Examples, every magnetic disk covered with the sputtered carbonaceous protective film of 20 nm in thickness was immersed in the surface-treating solutions for 10 minutes, pulled up at a rate of 0.5 cm/min and dried. Thereafter, the magnetic disk was irradiated with 25 mW ultraviolet ray having a wavelength of 365 nm from a 500 W high-pressure mercury lamp in a nitrogen atmosphere. Thus, the desired lubricating film was formed.

Thereafter, for the purpose of the life test, the disk was immersed in a fluorine-containing solvent having a boiling point of 100° C. and rinsed by ultrasonic wave irradiation.

The film thickness of the lubricant was measured by means of FT-IR. After the contact.start.stop (CSS) test was carried out at a peripheral speed of 20 m/sec with a load of 20 g applied by point contant, the frictional force was measured. These results are shown in Table 2.

TABLE 2

| Example | Compound | Durability test for lubricating film | |
|---|---|---|---|
| | | Ultrasonic wave rinsing | CSS test (10000 times) |
| 34 | (9) | ○ | ⊙ |
| 35 | (10) | ○ | ⊙ |
| 36 | (11) | ○ | ⊙ |
| 37 | (12) | ○ | ○ |
| 38 | (13) | ○ | ⊙ |
| 39 | (14) | ○ | ⊙ |
| 40 | (15) | ○ | ⊙ |
| 41 | (16) | ○ | ○ |
| 42 | (39) | ○ | ○ |
| 43 | (40) | ○ | ⊙ |
| 44 | (41) | ○ | ⊙ |
| 45 | (43) | ○ | ○ |
| 46 | (44) | ○ | ⊙ |
| 47 | (45) | ○ | ⊙ |
| 48 | (48) | ○ | ○ |
| 49 | (49) | ○ | ⊙ |
| 50 | (50) | ○ | ⊙ |
| 51 | (51) | ○ | ○ |
| 52 | (52) | ○ | ⊙ |
| 53 | (53) | ○ | ⊙ |
| 54 | (56) | ○ | ○ |
| 55 | (57) | ○ | ⊙ |
| 56 | (58) | ○ | ⊙ |
| 57 | (59) | ○ | ○ |
| 58 | (60) | ○ | ⊙ |
| 49 | (61) | ○ | ⊙ |
| 60 (Reference) | (62) | ○ | ○ |
| 61 | (63) | ○ | ○ |
| 62 | (64) | ○ | ○ |
| 63 | (65) | ○ | ○ |
| 64 | (66) | ○ | ○ |
| 65 | (67) | ○ | ○ |

Examples 66 to 97

Every magnetic disk, 5 inches in diameter, covered with an amorphous carbonaceous protective film of 20 nm in film thickness previously formed by the CVD method was immersed for 10 minutes in the same surface-treating solutions as used in Examples 1 to 32, taken out of the solutions and dried. The disk thus coated with the surface-treating agent was heat-treated at 120° C. for 30 minutes in place of exposure to ultraviolet ray to allow the denitrogenation reaction to occur. Thus, a lubricating film was formed on the carbonaceous protective film. For the purpose of the life test, the disk was immersed in a fluorine-containing solvent having a boiling point of 100° C. and rinsed by ultrasonic wave irradiation. The film thickness of the lubricant was measured by means of FT-IR. After the contact.start.stop (CSS) test was carried out at a peripheral speed of 20 m/sec with a load of 20 g applied by point contact, the frictional force was measured. These results are shown in Table 3.

TABLE 3

| Example | Compound | Durability test for lubricating film | |
|---|---|---|---|
| | | Ultrasonic wave rinsing | CSS test (10000 times) |
| 66 | (9) | O | O |
| 67 | (10) | O | O |
| 68 | (11) | O | O |
| 69 | (12) | O | O |
| 70 | (13) | O | O |
| 71 | (14) | O | O |
| 72 | (15) | O | O |
| 73 | (16) | O | O |
| 74 | (39) | O | O |
| 75 | (40) | O | O |
| 76 | (41) | O | O |
| 77 | (43) | O | O |
| 78 | (44) | O | O |
| 79 | (45) | O | O |
| 80 | (48) | O | O |
| 81 | (49) | O | O |
| 82 | (50) | O | O |
| 83 | (51) | O | O |
| 84 | (52) | O | O |
| 85 | (53) | O | O |
| 86 | (56) | O | O |
| 87 | (57) | O | O |
| 88 | (58) | O | O |
| 89 | (59) | O | O |
| 90 | (60) | O | O |
| 91 | (61) | O | O |
| 92 (Reference) | (62) | O | O |
| 93 | (63) | O | O |
| 94 | (64) | O | O |
| 95 | (65) | O | O |
| 96 | (66) | O | O |
| 97 | (67) | O | O |

Comparative Example 1

The lubricant A, $F-(CF_2CF_2CF_2O)_n-CF_2CF_2COOCH_2CF_2CF_3$, (the ester of perfluoropolyethercarboxylic acid (Demnum SY-3) having a repeating structure of $R_{f1}$ produced by DAIKIN INDUSTRIES, LTD.) regarded as the best article among the commercially available ones, was dissolved in fluorine-containing solvent having a boiling point of 100° C. to prepare a 1 wt. % solution. This solution was coated onto a magnetic disk protected with a sputtered carbonaceous film and dried. The magnetic disk was then immersed in the above solvent and irradiated with ultrasonic wave. This sample was measured for the thickness of film of the lubricant and frictional force. The results are collectively shown in Table 4.

Comparative Example 2

Procedure was carried out in the same manner as in Comparative Example 1 except that the commercially available lubricant A was replaced by a lubricant B (a perfluoropolyethercarboxylic acid (Krytox 157FS) produced by Du Pont,

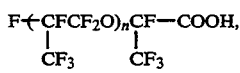

its perfluoropolyether portion having a repeating structure of $R_{f2}$). The results are collectively shown in Table 4.

Comparative Example 3

Procedure was carried out in the same manner as in Comparative Example 1 except that the commercially available lubricant A was replaced by a lubricant C (a perfluoropolyetheralcohol (Fomblin Z DOL) produced by Montefluos S.p.A. $HOCH_2CF_2-(OC_2F_4)_k-(OCF_2)_l-OCF_2CH_2OH$, its perfluoropolyether portion having a repeating structure of $R_{f4}$). The results are collectively shown in Table 4.

TABLE 4

| Comparative Example | Compound | Durability test for lubricating film | |
|---|---|---|---|
| | | Ultrasonic wave rinsing | CSS test (10000 times) |
| 1 | Lubricant A (Demnum SY-3) | X | X |
| 2 | Lubricant B (Krytox 157FS) | X | X |
| 3 | Lubricant C (Fomblin Z DOL) | X | X |

As apparent from these results, the azide compounds of the present invention, as shown in Tables 1 to 3, have a film thickness retention of 80% or more after ultrasonic wave rinsing, a small static friction coefficient even after the CSS test repeated 10000 times and excellent adhesion property and durability. On the other hand, the results of Comparative Examples 1 to 3 showed that the known lubricants have no good adhesion property and durability as are shown by a lowering in the rate of fixation of the lubricating film after ultrasonic wave rinsing and a rise in the static friction coefficient after the CSS test repeated 10000 times.

Example 98

Floppy disks were used in place of magnetic disks as the material to be treated, and the same lubricating film as in the above Examples was formed on the magnetic film. The results showed that the same good lubricating film as in the above Examples can be formed.

Example 99

A separator for two-side adhesive tapes was used in place of magnetic disks as the material to be treated, and the same lubricating film as in the above Examples was formed on the surface of the separator. The results showed that the same good lubricating film as in the above Examples can be formed. This separator is one preventing both the adhesive surfaces of the tape from adhering to each other when the tape is wound on a reel.

Example 100

A mold used in molding plastics was used in place of magnetic disks as the material to be treated, and the same lubricating film as in the above Examples was formed on the surface of the mold. The results showed that the same good lubricating film as in the above Examples can be formed. The lubricating film of the present invention has heat resistance and release property which makes the surface of the mold difficult to become wet, so that a mold having excellent durability could be realized.

Examples 101 to 152

(1) Synthesis of lubricant

Carboxylic acids having a fluoroalkylpolyether group represented by the formulae 69 and 70 were separately treated with an equimolar amount of phosphorus pentachloride to obtain the respective acid chlorides,

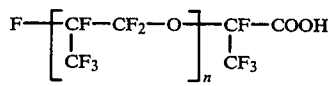 (69)

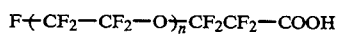 (70)

wherein n is 20 to 30.

Thereafter, every acid chloride thus obtained was reacted with each of the azide compounds (71) to (88) shown in Tables 5 and 6 [compounds (71) to (78) and (87) and (88) are an aromatic azide, and compounds (79) to (86) are an aromatic sulfoneazide)]. The resulting products were after-treated and purified to obtain compounds represented by the formulae (17) to (22) in a yield of 25 to 78%. Symbols R and $R_f$ in the formulae (17) to (22) are as shown in Tables 7 and 8. Lubricants (1) to (36) containing as a main component the azide compounds having a fluoroalkylpolyether group were obtained.

TABLE 5

| Compound No. | Aromatic azide compound |
|---|---|
| 71 | $N_3$—⌬—C(=O)—OCH$_2$CH$_2$—OH |
| 72 | $N_3$—⌬—CH=CH—C(=O)—O—CH$_2$CH$_2$—OH |
| 73 | $N_3$—⌬—CH=C(CN)—C(=O)—O—CH$_2$CH$_2$—OH |
| 74 | $N_3$—⌬—CH=CH—C(=O)—⌬—CH$_2$CH$_2$OH |
| 75 | $N_3$—⌬—C(=O)—OCH$_2$CH$_2$—NH$_2$ |
| 76 | $N_3$—⌬—CH=CH—C(=O)—O—CH$_2$CH$_2$—NH$_2$ |
| 77 | $N_3$—⌬—CH=C(CN)—C(=O)—O—CH$_2$CH$_2$—NH$_2$ |
| 78 | $N_3$—⌬—CH=CH—C(=O)—⌬—CH$_2$CH$_2$NH$_2$ |
| 87 | $N_3$—⌬—CH=CH—CH=[cyclohexanone-4-OH]=CH—CH=CH—⌬—$N_3$ |

TABLE 5-continued

| Compound No. | Aromatic azide compound |
|---|---|
| 88 | N₃—⟨C₆H₄⟩—CH=CH—CH=⟨cyclohexanone with CH₂OH⟩=CH—CH=CH—⟨C₆H₄⟩—N₃ (cyclohexanone bears =O and CH₂OH substituent) |

TABLE 6

| Compound No. | Aromatic sulfoneazide compound |
|---|---|
| 79 | N₃SO₂—⟨C₆H₄⟩—C(=O)—OCH₂CH₂—OH |
| 80 | N₃SO₂—⟨C₆H₄⟩—CH=CH—C(=O)—O—CH₂CH₂—OH |
| 81 | N₃SO₂—⟨C₆H₄⟩—CH=C(CN)—C(=O)—O—CH₂CH₂—OH |
| 82 | N₃SO₂—⟨C₆H₄⟩—CH=CH—C(=O)—⟨C₆H₄⟩—CH₂CH₂OH |
| 83 | N₃SO₂—⟨C₆H₄⟩—C(=O)—OCH₂CH₂—NH₂ |
| 84 | N₃SO₂—⟨C₆H₄⟩—CH=CH—C(=O)—O—CH₂CH₂—NH₂ |
| 85 | N₃SO₂—⟨C₆H₄⟩—CH=C(CN)—C(=O)—O—CH₂CH₂—NH₂ |
| 86 | N₃SO₂—⟨C₆H₄⟩—CH=CH—C(=O)—⟨C₆H₄⟩—CH₂CH₂NH₂ |

TABLE 7

| Formula | | $R_1$ | $R_2$ | $R_3$ | $R_4$ |
|---|---|---|---|---|---|
| 17 | $R_{f1}'$ | Lubricant 1 | Lubricant 2 | Lubricant 3 | Lubricant 4 |
|    | $R_{f2}'$ | Lubricant 5 | Lubricant 6 | Lubricant 7 | Lubricant 8 |
| 18 | $R_{f1}'$ | Lubricant 9 | Lubricant 10 | Lubricant 11 | Lubricant 12 |
|    | $R_{f2}'$ | Lubricant 13 | Lubricant 14 | Lubricant is | Lubricant 16 |
| 19 | $R_{f1}'$ | Lubricant 17 | Lubricant 18 | Lubricant 19 | Lubricant 20 |
|    | $R_{f2}'$ | Lubricant 21 | Lubricant 22 | Lubricant 23 | Lubricant 24 |
| 20 | $R_{f1}'$ | Lubricant 25 | Lubricant 26 | Lubricant 27 | Lubricant 28 |
|    | $R_{f2}'$ | Lubricant 29 | Lubricant 30 | Lubricant 31 | Lubricant 32 |

In Table 7, $R_1$ to $R_4$ representing a divalent organic group having an ester bond and $R_{f1}'$ and $R_{f2}'$ representing a fluoroalkylpolyether group are as follows:

$R_1$: —COOCH$_2$CH$_2$—, $R_2$: —CH=CHCOOCH$_2$CH$_2$—, $R_3$: —CH=C(CN)COOCH$_2$CH$_2$—, $R_4$: —CH=CHCOOC$_6$H$_4$CH$_2$CH$_2$—

$R_{f1'}$: —CF—[OCF$_2$CF(CF$_3$)]$_n$—F,
       |
       CF$_3$ $R_{f2'}$: —CF$_2$CF$_2$—(OCF$_2$CF$_2$CF$_2$)$_n$—F wherein n is 20 to 30.

TABLE 8

| Formula | $R_{f1'}$ | $R_{f2'}$ |
|---|---|---|
| 21 | Lubricant 33 | Lubricant 34 |
| 22 | Lubricant 35 | Lubricant 36 |

In Table 8, $R_{f1'}$ and $R_{f2'}$ representing a fluoroalkylpolyether group are as follows:

$R_{f1'}$: —CF—[OCF$_2$CF(CF$_3$)]$_n$—F,
       |
       CF$_3$ $R_{f2'}$: —CF$_2$CF$_2$—(OCF$_2$CF$_2$CF$_2$)$_n$—F wherein n is 20 to 30.

Similarly, a carboxylic acid having a fluoroalkylpolyether group represented by the formula 31, HOOC(CF$_2$CF$_2$O)$_k$—(CF$_2$O)$_l$—COOH     (31)

wherein both k and l are 20 to 30, was converted to the acid chloride which was then reacted with each of azide compounds (13) to (28) shown in Tables 1 and 2 to obtain lubricants represented by the formulae 7 to 10 in a yield of 28 to 69%.

A symbol R in the formulae are as shown in Table 9. Lubricants (37) to (52) containing as a main component azide compounds having a fluoroalkylpolyether group were obtained.

TABLE 9

| Formula | $R_1$ | $R_2$ | $R_3$ | $R_4$ |
|---|---|---|---|---|
| 23 | Lubricant 37 | Lubricant 38 | Lubricant 39 | Lubricant 40 |
| 24 | Lubricant 41 | Lubricant 42 | Lubricant 43 | Lubricant 44 |
| 25 | Lubricant 45 | Lubricant 46 | Lubricant 47 | Lubricant 48 |
| 26 | Lubricant 49 | Lubricant 50 | Lubricant 51 | Lubricant 52 |

In Table 9, symbols $R_1$ to $R_4$ representing divalent organic groups having an ester bond are as follows:

$R_1$: —COOCH$_2$CH$_2$—, $R_2$: —CH=CHCOOCH$_2$CH$_2$—, $R_3$: —CH=C(CN)COOCH$_2$CH$_2$—, $R_4$: —CH=CHCOOC$_6$H$_4$CH$_2$CH$_2$—.

Figure 3:
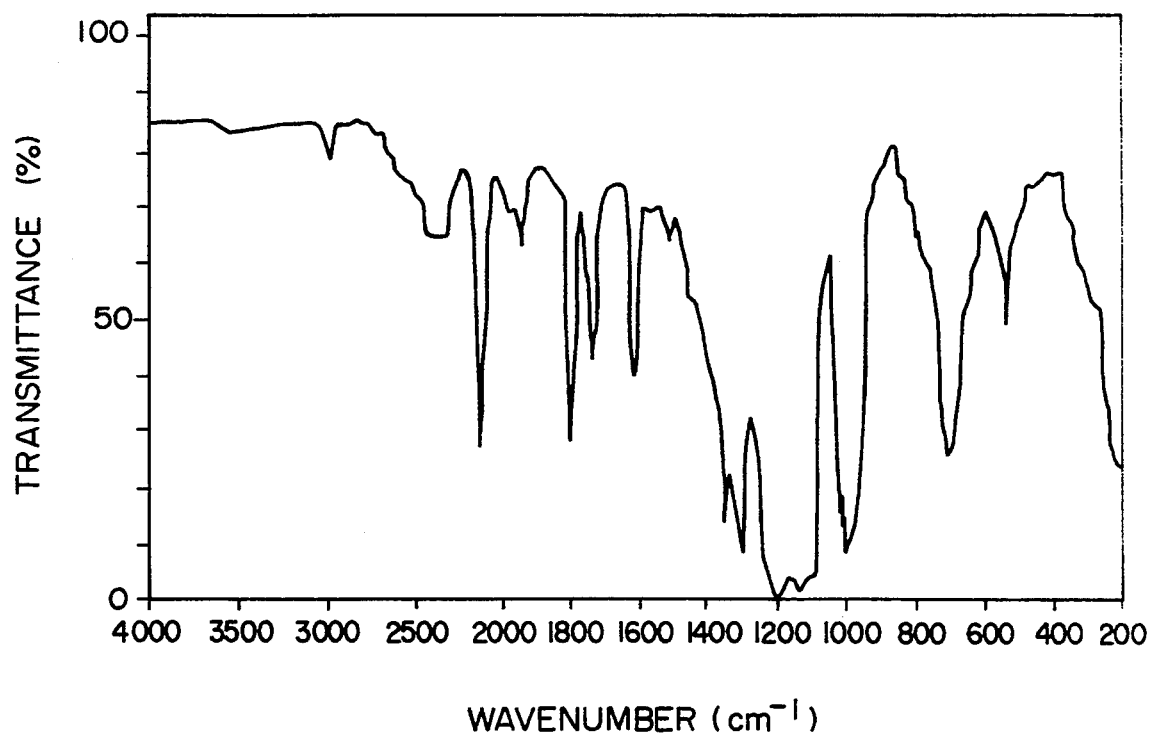
FIG. 3 shows the IR spectrum of the azide compound of the present invention represented by the formula 17.
Figure 5:
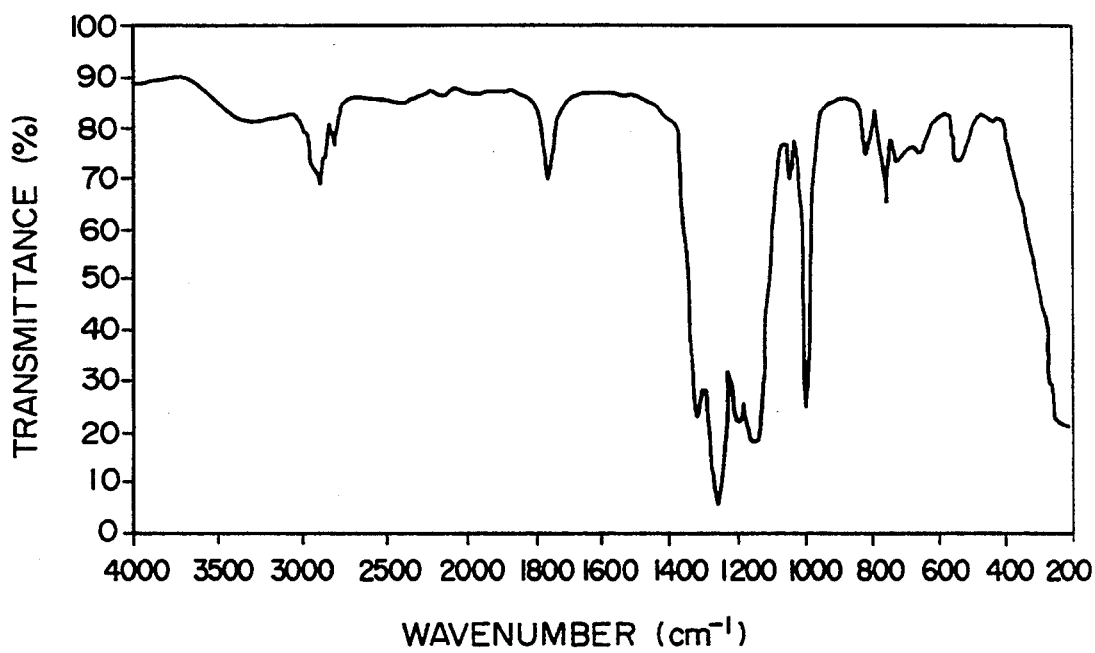
FIG. 5 shows the IR spectrum of the compound of the present invention represented by the formula 27.

Among the azide compounds, the typical infrared absorption spectrum of the azide compound of the formula 17 is shown in FIG. 3.

(2) Formation of lubricating film and evaluation of its characteristics

① Preparation of material to be treated

The material to be treated used here to coat the lubricant of the present invention is a magnetic recording medium having a sectional structure shown in FIG. 2. This magnetic recording medium is a magnetic disk of which the surface has previously been coated with a carbonaceous protective film. Referring to the constitution of the magnetic disk according to the drawing, the magnetic disk has a structure that a ground layer (2) such as Ni-P and a magnetic film (3) are vacuum-deposited in this order onto a non-magnetic substrate (1) such as Al, and further a carbonaceous protective film (4) is applied thereto by the sputtering method or plasma CVD method. In the sputtering method, the carbonaceous protective film is formed as follows: A magnetic disk is placed in a vacuum of 10$^{-6}$ Torr or more, an argon gas (gas pressure, 10 mTorr) is introduced into the vacuum and sputtering is carried out with graphite as a target. The plasma CVD method (chemical vaporing deposition) refers to a method of forming a thin film by the reaction on substrate of ions or radicals produced by electrolytic dissociation or plasma reaction of a gas used as material. The protective film formed by this method has a property that it has high hardness, transparency and resistance and is chemically inactive.

② Formation of lubricating film on material to be treated

Three grams of each of the lubricants (1) to (52) synthesized by the above methods was dissolved in 27 g of a fluorine-containing solvent having a boiling point of 100° C. to prepare a 1 wt. % solution. These solutions were used as a lubricant solution. The solvent used was a perfluorocarbon oil, Fluorinert (trade name of Sumitomo 3M Co.).

Magnetic disks, 5 inches in diameter, covered with an amorphous carbonaceous protective film of 20 nm in film thickness previously formed by the CVD method, were prepared for. Every magnetic disk was immersed in the above lubricant solutions for 10 minutes, pulled up at a rate of 0.5 cm/min while irradiating the disk with 25 mW ultraviolet ray having a wavelength of 365 nm from a 500 W high-pressure mercury lamp in a nitrogen atmosphere using an apparatus shown in FIG. 4, and then dried. Thus, formation of a lubricating film on the carbonaceous protective film was finished. Thereafter, for the purpose of the subsequent evaluation test, the disk was immersed in a fluorine-containing solvent having a boiling point of 100° C. and rinsed by ultrasonic wave irradiation. At that time, the lubricant retention was indicated by ○ for 80% or more and indicated by x for less than 80%.

The coating apparatus shown in FIG. 4 will be explained. 45 is an apparatus for putting the magnetic disk up and down constituting a part of a conveying means. One end of a wire 42 is connected to a motor (not shown) and the other end thereof is connected to a holder 43 for a material to be treated through a sheave 44. The material to be treated 41 (magnetic disk) held by the holder 43 is introduced into a lubricant-storing vessel 48 filled with a lubricant solution, immersed in the solution and then pulled up at an optional definite speed by means of the apparatus 45. The material in the holder, when pulled up from the lubricant solution, is in a condition that it has been covered with the film of the lubricant. 40 is a reaction vessel connected to the opening of the lubricant-storing vessel 48, and the hollow portion of the reaction vessel is a reaction room of which the periphery is equipped with a high-pressure mercury lamp 46. This mercury lamp 46 is a means for allowing the lubricant coated onto the surface of the material 41 to cause the denitrogenation reaction. Further, this reaction room is equipped with a nitrogen gas-feeding apparatus 47 which is a gas-introducing means for filling the reaction room with a non-oxidizing gas.

The material to be treated 41 coated with the lubricant undergoes the denitrogenation reaction while it moves at a definite speed in the reaction room of the reaction vessel 40, and the coating film causes reaction to turn lubricating film strongly adhered to the material 41. The non-oxidizing gas may be any of those which cause no oxidation of the lubricant. A nitrogen gas was used here, but other inert gases may be used. A means to cause the denitrogenation reaction used here was to expose either side of the material to be treated to ultraviolet ray from a 500 W high-pressure mercury lamp. The ultraviolet ray from a high-pressure mercury lamp matches well with a wavelength which allows the azide compound of the present invention to cause photoreaction, so that it is practically preferred.

③ Evaluation of characteristics

The film thickness of the lubricating film was measured using a Fourier transformation infrared spectrophotometer (abbreviated as FT-IR), and the static friction coefficient was measured by applying a load of 20 g to this sample by point contact. Also, the abrasion of the lubricating film covering the magnetic disk was measured by carrying out the contact-start-stop (CSS) test at a peripheral speed of 20 m/sec with a load of 20 g applied to the magnetic disk by point contact. The results are shown in Tables 10 to 12.

TABLE 10[1]

| Example | Lubricant | Lubricant retention after ultrasonic wave rinsing | Static friction coefficient | Abrasion by CSS test |
|---|---|---|---|---|
| 101 | 1 | ○ | 0.13 or less | Not observed |
| 102 | 2 | " | " | " |
| 103 | 3 | " | " | " |
| 104 | 4 | " | " | " |
| 105 | 5 | " | " | " |
| 106 | 6 | " | " | " |
| 107 | 7 | " | " | " |
| 108 | 8 | " | " | " |
| 109 | 9 | " | " | " |
| 110 | 10 | " | " | " |
| 111 | 11 | " | " | " |
| 112 | 12 | " | " | " |
| 113 | 13 | " | " | " |
| 114 | 14 | " | " | " |
| 115 | 15 | " | " | " |
| 116 | 16 | " | " | " |
| 117 | 17 | " | " | " |
| 118 | 18 | " | " | " |
| 119 | 19 | " | " | " |
| 120 | 20 | " | " | " |
| 121 | 21 | " | " | " |
| 122 | 22 | " | " | " |
| 123 | 23 | " | " | " |
| 124 | 24 | " | " | " |
| 125 | 25 | " | " | " |
| 126 | 26 | " | " | " |
| 127 | 27 | " | " | " |
| 128 | 28 | " | " | " |

TABLE 10[1]-continued

| Example | Lubricant | Lubricant retention after ultrasonic wave rinsing | Static friction coefficient | Abrasion by CSS test |
|---|---|---|---|---|
| 129 | 29 | " | " | " |
| 130 | 30 | " | " | " |
| 131 | 31 | " | " | " |
| 132 | 32 | " | " | " |
| Target value | | " | 0.15 or less | " |

[1]: Lubricating films with the compounds (17) to (20) were formed on the carbonaceous protective films formed by the CVD method.

TABLE 11[2]

| Example | Lubricant | Lubricant retention after ultrasonic wave rinsing | Static friction coefficient | Abrasion by CSS test |
|---|---|---|---|---|
| 133 | 33 | ○ | 0.13 or less | Not observed |
| 134 | 34 | " | " | " |
| 135 | 35 | " | " | " |
| 136 | 36 | " | " | " |
| Target value | | " | 0.15 or less | " |

[2]: Lubricating films with the compounds (21) and (22) were formed on the carbonaceous protective films formed by the CVD method.

TABLE 12[3]

| Example | Lubricant | Lubricant retention after ultrasonic wave rinsing | Static friction coefficient | Abrasion by CSS test |
|---|---|---|---|---|
| 137 | 37 | ○ | 0.13 or less | Not observed |
| 138 | 38 | " | " | " |
| 139 | 39 | " | " | " |
| 140 | 40 | " | " | " |
| 141 | 41 | " | " | " |
| 142 | 42 | " | " | " |
| 143 | 43 | " | " | " |
| 144 | 44 | " | " | " |
| 145 | 45 | " | " | " |
| 146 | 46 | " | " | " |
| 147 | 47 | " | " | " |
| 148 | 48 | " | " | " |
| 149 | 49 | " | " | " |
| 150 | 50 | " | " | " |
| 151 | 51 | " | " | " |
| 152 | 52 | " | " | " |
| Target value | | " | 0.15 or less | " |

[3]: Lubricating films with the compounds (23) to (26) were formed on the carbonaceous protective films formed by the CVD method In Examples described above, magnetic disks covered with the amorphous carbonaceous protective film formed by the CVD method were used as the material to be treated. In the following Examples 153 to 168, magnetic disks covered with the carbonaceous protective film formed by the sputtering method were used.

Examples 153 to 168

Figure 4:
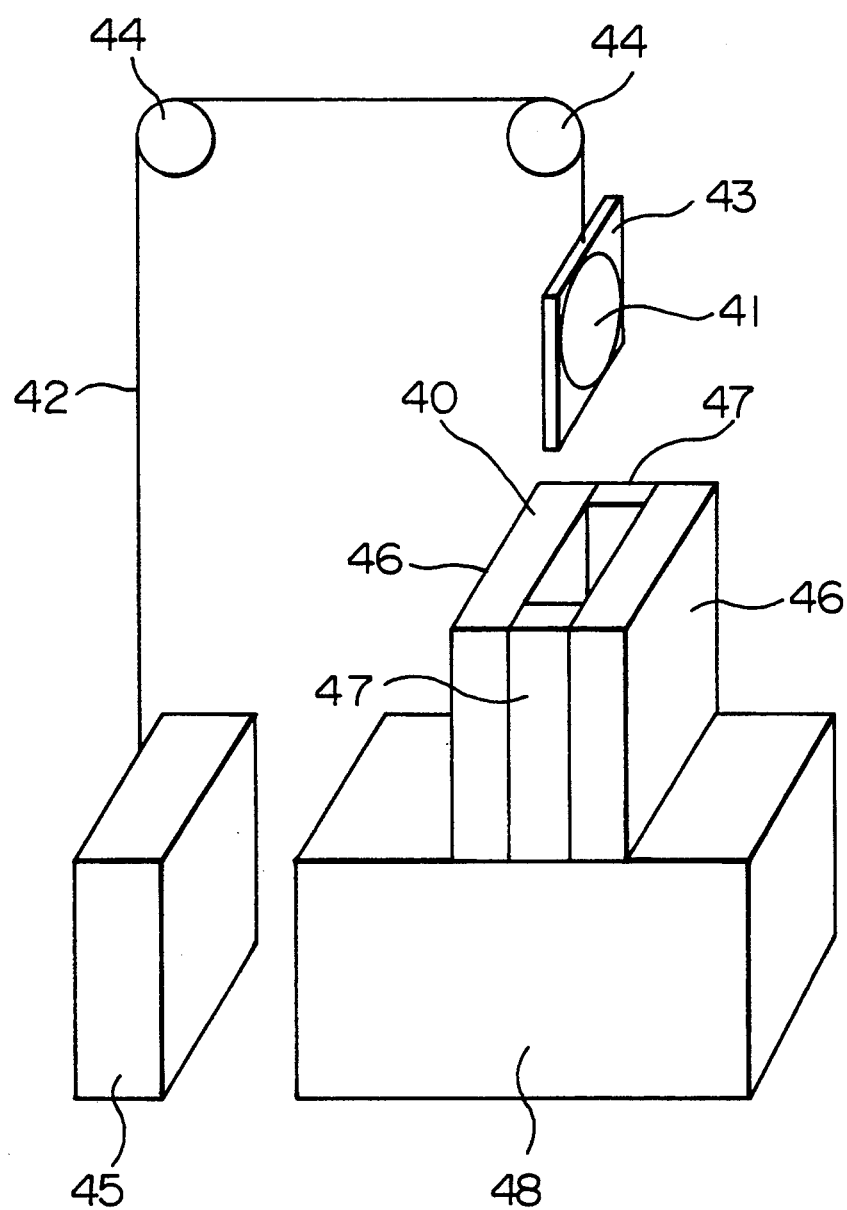
FIG. 4 shows a notional view of an apparatus for coating the photo-reactive lubricant.

In the same manner as in the foregoing Examples, every magnetic disk covered with the sputtered carbonaceous protective film of 20 nm in thickness was immersed for 10 minutes in each of solutions containing the lubricants (1) to (16), pulled up at a rate of 0.5 cm/min while irradiating the disk with 25 mW ultraviolet ray having a wavelength of 365 nm from a 500 W high-pressure mercury lamp in a nitrogen atmosphere using an apparatus shown in FIG. 4, and then dried. Thus, the desired lubricating films were formed.

Thereafter, for the purpose of the evaluation test, the disk was immersed in a fluorine-containing solvent having a boiling point of 100° C. and rinsed by ultrasonic wave irradiation.

The film thickness of the lubricating film was measured using a FT-IR, and the static friction coefficient was measured by applying a load of 20 g of this sample by point contact. Also, the abrasion of the lubricating film covering the magnetic disk was measured by carrying out the contact.start.stop (CSS) test at a peripheral speed of 20 m/sec with a load of 20 g applied to the magnetic disk by point contact. The results are shown in Table 13.

TABLE 13[4)]

| Example | Lubricant | Lubricant retention after ultrasonic wave rinsing | Static friction coefficient | Abrasion by CSS test |
|---|---|---|---|---|
| 153 | 1 | ○ | 0.13 or less | Not observed |
| 154 | 2 | " | " | " |
| 155 | 3 | " | " | " |
| 156 | 4 | " | " | " |
| 157 | 5 | " | " | " |
| 158 | 6 | " | " | " |
| 159 | 7 | " | " | " |
| 160 | 8 | " | " | " |
| 161 | 9 | " | " | " |
| 162 | 10 | " | " | " |
| 163 | 11 | " | " | " |
| 164 | 12 | " | " | " |
| 165 | 13 | " | " | " |
| 166 | 14 | " | " | " |
| 167 | 15 | " | " | " |
| 168 | 16 | " | " | " |
| Target value | | " | 0.15 or less | " |

[4)]: Lubricating films with the compounds (17) to (20) were formed on the sputtered carbonaceous protective films.

Examples 169 to 184

Every magnetic disk, 5 inches in diameter, covered with an amorphous carbonaceous protective film of 20 nm in film thickness formed by the CVD method was immersed for 10 minutes in the same solutions containing the lubricants (1) to (16) as used in Examples 101 to 116, taken out of the solutions and dried. The magnetic disk thus coated with the lubricant was heat-treated at 120° C. for 30 minutes in place of exposure to ultraviolet ray to cause the denitrogenation reaction to occur. Thus, a lubricating film was formed. For the purpose of the life test, the magnetic disk was immersed in a fluorine-containing solvent having a boiling point of 100° C. and rinsed by ultrasonic wave irradiation. The thickness of the lubricating film was measured by means of FT-IR, and the static friction coefficient was measured by applying a load of 20 g to this sample by point contact. Also, the abrasion of the lubricating film covering the magnetic disk was measured by carrying out the contact.start.stop (CSS) test at a peripheral speed of 20 m/sec with a load of 20 g applied to the magnetic disk by point contact. The results are shown in Table 14. The values of the static friction coefficient are good as a value of 0.15 or less shows, although they are a little larger than those (0.13 or less) in Examples 101 to 116.

TABLE 14[5)]

| Example | Lubricant | Lubricant retention after ultrasonic wave rinsing | Static friction coefficient | Abrasion by CSS test |
|---|---|---|---|---|
| 169 | 1 | ○ | 0.15 or less | Not observed |
| 170 | 2 | " | " | " |
| 171 | 3 | " | " | " |
| 172 | 4 | " | " | " |
| 173 | 5 | " | " | " |
| 174 | 6 | " | " | " |
| 175 | 7 | " | " | " |
| 176 | 8 | " | " | " |
| 177 | 9 | " | " | " |
| 178 | 10 | " | " | " |
| 179 | 11 | " | " | " |
| 180 | 12 | " | " | " |
| 181 | 13 | " | " | " |
| 182 | 14 | " | " | " |
| 183 | 15 | " | " | " |
| 184 | 16 | " | " | " |
| Target value | | " | " | " |

[5)]: Lubricating films with the compounds (17) to (20) were formed by heat-treatment on the carbonaceous protective films formed by the CVD method.

Comparative Example 4

A lubricant F$\text{-(CF}_2\text{CF}_2\text{CF}_2\text{O)}_{\overline{n}}\text{CF}_2\text{CF}_2\text{COOCH}_2\text{CF}_2\text{CF}_3$ (the ester of a perfluoropolyethercarboxylic acid (Demnum SY-3) produced by DAIKIN INDUSTRIES, LTD.) regarded as the best article among the commercially available ones, was dissolved in a fluorine-containing solvent having a boiling point of 100° C. to prepare a 1 wt. % solution. This solution was coated onto a magnetic disk protected with a sputtered carbonaceous film and dried. The magnetic disk was then immersed in the above solvent and irradiated with ultrasonic wave. This sample was measured for the thickness of film of the lubricant, static friction coefficient and abrasion. The results are collectively shown in Table 15.

Comparative Example 5

Procedure was carried out in the same manner as in Comparative Example 4 except that the commercially available lubricant was replaced by a perfluoropolyethercarboxylic acid (Krytox 157FS) produced by Du Pont

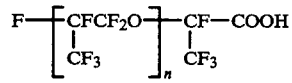

the repeating structure of the perfluoropolyether portion is a little different from that of the perfluoropolyether portion of the above lubricant produced by DAIKIN INDUSTRIES, LTD.). The results are collectively shown in Table 15.

Comparative Example 6

Procedure was carried out in the same manner as in Comparative Example 4 except that the commercially available lubricant was replaced by the ester of a perfluoropolyetheralcohol (Fomblin Z DOL) produced by Montefluos S.p.A. $\text{HOCH}_2\text{CF}_2\text{-(OC}_2\text{F}_4)_k(\text{OCF}_2)_l\text{—OCF}_2\text{CH}_2\text{OH}$ (the repeating structure of the perfluoropolyether portion is a little different from that of the perfluoropolyether portion of the above lubricants produced by DAIKIN INDUSTRIES, LTD. and Du Pont). The results are collectively shown in Table 15.

TABLE 15[6)]

| Comparative Example | Lubricant | Lubricant retention after ultrasonic wave rinsing | Static friction coefficient | Abrasion by CSS test |
|---|---|---|---|---|
| 4 | Lubricant A (Demnum SY-3) | X | 0.20 or more | Observed |
| 5 | Lubricant B (Krytox 157FS) | " | 0.20 or more | " |
| 6 | Lubricant C (Fomblin Z DOL) | " | 0.20 or more | " |

[6)]: Commercially available lubricants were coated onto the sputtered carbonaceous protective film.

As apparent from these results, the azide compounds of the present invention, as shown in Table 13, give a lubricating film having a film thickness retention of 80% or more after ultrasonic wave rinsing, a small static friction coefficient even after the CSS test repeated 10000 times and excellent adhesion property and durability. On the other hand, the results of Comparative Examples 4 to 6 showed that the known lubricants have no good adhesion property and durability as are shown by a lowering in the rate of fixation of the lubricating film after ultrasonic wave rinsing and a rise in the static friction coefficient after the CSS test repeated 10000 times.

Example 185

Floppy disks were used in place of magnetic disks as the material to be treated, and the same lubricating film as in the above Examples was formed on the magnetic film. The results showed that the same good lubricating film as in the above Examples can be formed.

Example 186

A separator for two-side adhesive tapes was used in place of magnetic disks as the material to be treated, and the same lubricating film as in the above Examples was formed on the surface of the separator. The results showed that the same good lubricating film as in the above Examples can be formed. This separator is one preventing both the adhesive surfaces of the tape from adhering to each other when the tape is wound on a reel.

Example 187

A mold used in molding plastics was used in place of magnetic disks as the material to be treated, and the same lubricating film as in the above Examples was formed on the surface of the mold. The results showed that the same good lubricating film as in the above Examples can be formed. The lubricating film of the present invention has heat resistance and release property (which makes the surface of the mold difficult to become wet), so that a mold having excellent durability could be realized.

Example 188

10.78 Grams (2.4 mmoles) of a perfluoropolyether-carboxylic acid represented by the formula 33 (average molecular weight, 4500) was dissolved in 10 ml of trifluorotrichloroethane. To the resulting solution was added 514 mg (2.5 mmoles) of phosphorus pentachloride, and the mixture was stirred for 1 hour. After adding 126 mg (2.5 mmoles) of hydrazine monohydrate thereto, 1 ml of triethylamine was slowly added. After stirring for 3 hours, the reaction solution was extracted with a solvent, and the resulting extract was washed with water and dried over $MgSO_4$, a drier. The dryer was filtered off, and the solvent was distilled off to obtain 7.54 g of diacylhydrazine represented by the formula 28.

Three grams of the compound of the formula 28 thus synthesized was dissolved in 27 g of a fluorine-containing solvent having a boiling point of 100° C. to prepare a 1 wt. % solution.

A magnetic disk, 5 inches in diameter, covered with the sputtered carbonaceous protective film of 20 nm in film thickness was immersed in the above solution for 10 minutes, taken out of the solution and dried. The magnetic disk thus coated with the lubricant was irradiated for 3 minutes with 25 mW ultraviolet ray having a wavelength of 366 nm from a 500 W high-pressure mercury lamp. This magnetic disk was immersed in a fluorine-containing solvent having a boiling point of 100° C. and then rinsed by ultrasonic wave irradiation. The thickness retention of film of the lubricant was measured by means of a FT-IR before and after rinsing by ultrasonic wave irradiation to find that the thickness retention of film was 80%. The static friction coefficient was measured by applying a load of 20 g to this sample by point contact to find that it was good as a very small value of 0.13 showed. Also, the abrasion of the lubricating film was measured by carrying out the contact.-start.stop (CSS) test at a peripheral speed of 20 m/sec with a load of 20 g applied to this sample by point contact. As a result, it was found that the abrasion was hardly observed even when the measurement was repeated 10000 times.

Example 189

A magnetic disk, 5 inches in diameter, covered with the sputtered carbonaceous protective film of 20 nm in film thickness was immersed for 10 minutes in the solution containing the compound of the formula 28 prepared in Example 188, taken out of the solution dried. The magnetic disk thus coated with the lubricating substance was heat-treated at 120° C. for 30 minutes. After this sample was rinsed with the solvent in the same manner as in Example 188, the film thickness retention was measured. Further, the static friction coefficient was measured with a load of 20 g applied to this sample by point contact, and the abrasion was measured by the CSS test repeated 10000 times. The results are collectively shown in Table 16.

TABLE 16

| | Method for foaming carbonaceous protective film | Treatment after coating of lubricant | Lubricant retention after ultrasonic wave rinsing | Static friction coefficient | Abrasion after CSS test repeated 1000 times |
|---|---|---|---|---|---|
| Example | Sputtering | Irradiation | ○ | 0.12 | Not observed |

TABLE 16-continued

| | Method for foaming carbonaceous protective film | Treatment after coating of lubricant | Lubricant retention after ultrasonic wave rinsing | Static friction coefficient | Abrasion after CSS test repeated 1000 times |
|---|---|---|---|---|---|
| 188 | | with 366 nm UV for 3 minutes | | | |
| Example 189 | Sputtering | Heating at 120° C. for 30 minutes | " | 0.11 | Not observed |
| Example 190 | Plasma CVD | Irradiation with 366 nm UV for 3 minutes | " | 0.13 | Not observed |
| Example 191 | Plasma CVD | Heating at 120° C. for 30 minutes | " | 0.12 | Not observed |
| Target value | | | " | 0.20 or less | Not observed |

Example 190

A magnetic disk, 5 inches in diameter, covered with an amorphous carbonaceous protective film of 20 nm in film thickness formed by the CVD method was immersed for 10 minutes in the solution containing the compound of the formula 28 prepared in Example 188, after which it was taken out of the solution and dried. The magnetic disk thus coated with the lubricant was irradiated for 3 minutes with 25 mW ultraviolet ray from a 500 W high-pressure mercury lamp. After this sample was rinsed with the solvent in the same manner as in Example 188, the film thickness retention was measured. Further, the static friction coefficient was measured with a load of 20 g applied to this sample by point contact, and the abrasion was measured by the CSS test repeated 10000 times. The results are collectively shown in Table 16.

Example 191

A magnetic disk, 5 inches in diameter, covered with an amorphous carbonaceous protective film of 20 nm in film thickness formed by the CVD method was immersed for 10 minutes in the solution containing the compound of the formula 28 prepared in Example 188, after which it was taken out of the solution and dried. The magnetic disk thus coated with the lubricant was heat-treated at 120° C. for 30 minutes. After this sample was rinsed with the solvent in the same manner as in Example 188, the film thickness retention was measured. Further, the static friction coefficient was measured with a load of 20 g applied to this sample by point contact, and the abrasion was measured by the CSS test repeated 10000 times. The results are collectively shown in Table 16.

Example 192

A perfluoropolyethercarboxylic acid represented by the formula 34 was converted as follows to diacylhydrazine by the same procedure as shown in Example 188:11.55 Grams (3.3 mmoles) of a perfluoropolyethercarboxylic acid of the formula 34 (average molecular weight, 3500) was dissolved in 10 ml of trifluorotrichloroethane. To the resulting solution was added 860 mg (4.1 mmoles) of phosphorus pentachloride, and the mixture was stirred for 1 hour. After adding 226 mg (4.5 mmoles) of hydrazine monohydrate thereto, 1 ml of triethylamine was slowly added. After stirring for 3 hours, the reaction solution was extracted with a solvent, and the resulting extract was washed with water and dried over $MgSO_4$, a dryer. The dryer was filtered off, and the solvent was distilled off to obtain 8.41 g of diacylhydrazine represented by the formula 27.

Examples 193 to 196

Three grams of the compound of the formula 27 thus synthesized was dissolved in 27 g of a fluorine-containing solvent having a boiling point of 100° C. to prepare a 1 wt. % solution. According to the methods shown in Examples 188 to 191, this solution was coated onto the magnetic disk and after-treated, and then the thickness retention of film of the lubricant, static friction coefficient and abrasion were measured. The results are collectively shown in Examples 193 to 196 of Table 17.

TABLE 17

| | Method for foaming carbonaceous protective film | Treatment after coating of lubricant | Lubricant retention after ultrasonic wave rinsing | Static friction coefficient | Abrasion after CSS test repeated 1000 times |
|---|---|---|---|---|---|
| Example 193 | Sputtering | Irradiation with 366 nm UV for 3 minutes | ○ | 0.13 | Not observed |
| Example 194 | Sputtering | Heating at 120° C. for 30 minutes | " | 0.11 | Not observed |
| Example 195 | Plasma CVD | Irradiation with 366 nm UV for 3 minutes | " | 0.13 | Not observed |
| Example 196 | Plasma CVD | Heating at 120° C. for 30 minutes | " | 0.12 | Not observed |
| Target | | | " | 0.20 or less | Not observed |

TABLE 17-continued

| Method for foaming carbonaceous protective film | Treatment after coating of lubricant | Lubricant retention after ultrasonic wave rinsing | Static friction coefficient | Abrasion after CSS test repeated 1000 times |
|---|---|---|---|---|
| value | | | | |
| Example 197 | | | | | and abrasion were measured. The results are collectively shown in Examples 198 to 201 of Table 18.

TABLE 18

| | Method for foaming carbonaceous protective film | Treatment after coating of lubricant | Lubricant retention after ultrasonic wave rinsing | Static friction coefficient | Abrasion after CSS test repeated 1000 times |
|---|---|---|---|---|---|
| Example 198 | Sputtering | Irradiation with 366 nm UV for 3 minutes | ○ | 0.13 | Not observed |
| Example 199 | Sputtering | Heating at 120° C. for 30 minutes | " | 0.13 | Not observed |
| Example 200 | Plasma CVD | Irradiation with 366 nm UV for 3 minutes | " | 0.13 | Not observed |
| Example 201 | Plasma CVD | Heating at 120° C. for 30 minutes | " | 0.12 | Not observed |
| Target value | | | " | 0.20 or less | Not observed |

On treating a perfluoropolyethercarboxylic acid of the formula 33 with phosphorus pentachloride and then adding for example stearic acid hydrazide thereto, one of the compounds represented by the formula 29 was synthesized.

Examples 198 to 201

A series of these compounds represented by the formula 29 were each dissolved in a fluorine-containing solvent having a boiling point of 100° C. to prepare a 1 wt. % solution. This solution was coated onto the magnetic disk and after-treated, and then the thickness retention of film of the lubricant, static friction coefficient

Examples 202 to 213

Each of the compounds represented by the formulae 30, 31 and 32 similarly synthesized was dissolved in a fluorine-containing solvent having a boiling point of 100° C. to prepare a 1 wt. % solution. Every solution was coated onto the magnetic disk and after-treated, and then the thickness retention of film of the lubricant, static friction coefficient and abrasion were measured. The results are collectively shown in Examples 202 to 205 of Table 19 for the compound (30), Examples 206 to 209 of Table 20 for the compound (31) and Examples 210 to 213 of Table 21 for the compound (32).

TABLE 19

| | Method for foaming carbonaceous protective film | Treatment after coating of lubricant | Lubricant retention after ultrasonic wave rinsing | Static friction coefficient | Abrasion after CSS test repeated 1000 times |
|---|---|---|---|---|---|
| Example 202 | Sputtering | Irradiation with 366 nm UV for 3 minutes | ○ | 0.12 | Not observed |
| Example 203 | Sputtering | Heating at 120° C. for 30 minutes | " | 0.11 | Not observed |
| Example 204 | Plasma CVD | Irradiation with 366 nm UV for 3 minutes | " | 0.13 | Not observed |
| Example 205 | Plasma CVD | Heating at 120° C. for 30 minutes | " | 0.12 | Not observed |
| Target value | | | " | 0.20 or less | Not observed |

TABLE 20

| | Method for foaming carbonaceous protective film | Treatment after coating of lubricant | Lubricant retention after ultrasonic wave rinsing | Static friction coefficient | Abrasion after CSS test repeated 1000 times |
|---|---|---|---|---|---|
| Example | Sputtering | Irradiation | ○ | 0.12 | Not observed |

TABLE 20-continued

| | Method for foaming carbonaceous protective film | Treatment after coating of lubricant | Lubricant retention after ultrasonic wave rinsing | Static friction coefficient | Abrasion after CSS test repeated 1000 times |
|---|---|---|---|---|---|
| 206 | | with 366 nm UV for 3 minutes | | | |
| Example 207 | Sputtering | Heating at 120° C. for 30 minutes | " | 0.11 | Not observed |
| Example 208 | Plasma CVD | Irradiation with 366 nm UV for 3 minutes | " | 0.12 | Not observed |
| Example 209 | Plasma CVD | Heating at 120° C. for 30 minutes | " | 0.11 | Not observed |
| Target value | | | " | 0.20 or less | Not observed |

TABLE 21

| | Method for foaming carbonaceous protective film | Treatment after coating of lubricant | Lubricant retention after ultrasonic wave rinsing | Static friction coefficient | Abrasion after CSS test repeated 1000 times |
|---|---|---|---|---|---|
| Example 210 | Sputtering | Irradiation with 366 nm UV for 3 minutes | ○ | 0.13 | Not observed |
| Example 211 | Sputtering | Heating at 120° C. for 30 minutes | " | 0.12 | Not observed |
| Example 212 | Plasma CVD | Irradiation with 366 nm UV for 3 minutes | " | 0.12 | Not observed |
| Example 213 | Plasma CVD | Heating at 120° C. for 30 minutes | " | 0.12 | Not observed |
| Target value | | | " | 0.20 or less | Not observed |

Comparative Example 7

A perfluoropolyether, a lubricant (Fomblin Z-DOL produced by Montefluos S.p.A.), was dissolved in a fluorine-containing solvent having a boiling point of 100° C. to prepare a 1 wt. % solution. This solution was coated onto a magnetic disk protected with a sputtered carbonaceous film, and after drying, it was immersed in the above solvent and irradiated with ultrasonic wave. This sample was measured for the thickness retention of film of the lubricant, static friction coefficient and abrasion. The results are collectively shown in Table 22.

Comparative Examples 8 to 11

In the same manner as in Examples 188 to 191, the solution prepared in Comparative Example 7 was coated onto a magnetic disk and after-treated, and then measured for the thickness retention of film of the lubricant, static friction coefficient and abrasion. The results are collectively shown in Comparative Examples 8 to 11 of Table 22.

TABLE 22

| | Method for foaming carbonaceous protective film | Treatment after coating of lubricant | Lubricant retention after ultrasonic wave rinsing | Static friction coefficient | Abrasion after CSS test repeated 1000 times |
|---|---|---|---|---|---|
| Comparative Example 7 | Sputtering | Rinsing only with solvent | X | 0.5 or more | observed |
| Comparative Example 8 | Sputtering | Irradiation with 366 nm UV for 3 minutes | " | " | " |
| Comparative Example 9 | Plasma CVD | Heating at 120° C. for 30 minutes | " | " | " |
| Comparative Example 10 | Plasma CVD | Irradiation with 366 nm UV for 3 minutes | " | " | " |
| Comparative Example 11 | Plasma CVD | Heating at 120° C. for 30 minutes | " | " | " |

Comparative Examples 12 to 16

Procedure was carried out in the same manner as in Comparative Examples 7 to 11 except that the lubricant shown in Comparative Example 7 was replaced by Krytox 240AC (produced by Du Pont Co.). The results are collectively shown in Comparative Examples 12 to 16 of Table 23.

TABLE 23

| | Method for foaming carbonaceous protective film | Treatment after coating of lubricant | Lubricant retention after ultrasonic wave rinsing | Static friction coefficient | Abrasion after CSS test repeated 1000 times |
|---|---|---|---|---|---|
| Comparative Example 12 | Sputtering | Rinsing only with solvent | X | 0.5 or more | observed |
| Comparative Example 13 | Sputtering | Irradiation with 366 nm UV for 3 minutes | " | " | " |
| Comparative Example 14 | Sputtering | Heating at 120° C. for 30 minutes | " | " | " |
| Comparative Example 15 | Plasma CVD | Irradiation with 366 nm UV for 3 minutes | " | " | " |
| Comparative Example 16 | Plasma CVD | Heating at 120° C. for 30 minutes | " | " | " |

Comparative Examples 17 to 21

Procedure was carried out in the same manner as in Comparative Examples 7 to 11 except that the lubricant shown in Comparative Example 7 was replaced by Demnum SY-3 (produced by DAIKIN INDUSTRIES, LTD.). The results are collectively shown in Comparative Examples 17 to 21 of Table 24.

TABLE 24

| | Method for foaming carbonaceous protective film | Treatment after coating of lubricant | Lubricant retention after ultrasonic wave rinsing | Static friction coefficient | Abrasion after CSS test repeated 1000 times |
|---|---|---|---|---|---|
| Comparative Example 17 | Sputtering | Rinsing only with solvent | X | 0.5 or more | observed |
| Comparative Example 18 | Sputtering | Irradiation with 366 nm UV for 3 minutes | " | " | " |
| Comparative Example 19 | Sputtering | Heating at 120° C. for 30 minutes | " | " | " |
| Comparative Example 20 | Plasma CVD | Irradiation with 366 nm UV for 3 minutes | " | " | " |
| Comparative Example 21 | Plasma CVD | Heating at 120° C. for 30 minutes | " | " | " |

As apparent from these results, the diacylhydrazine lubricants of the present invention give a lubricating film having a good thickness retention of 80% or more after ultrasonic wave rinsing, a small static friction coefficient of 0.15 or less and excellent adhesion property and durability resisting the abrasion test repeated 10000 times. On the other hand, the known lubricants give no good results in any of the film thickness retention, static friction coefficient and abrasion.

What is claimed is:

1. A diacylhydrazine having at least one fluoroalkyl-polyether group as a side chain, selected from the group consisting of:

I: a diacylhydrazine having an average molecular weight of 500 to 20,000 and represented by the formula 27

(27)

II: a diacylhydrazine having an average molecular weight of 500 to 20,000 and represented by the formula 28

(28)

III: a diacylhydrazine having an average molecular weight of 500 to 20,000 and represented by the formula 29

(29)

wherein R represents one member selected from the group consisting of a hydrogen atom, an alkyl group and an aromatic group;

IV: a diacylhydrazine having an average molecular weight of 500 to 20,000 and represented by the formula 30

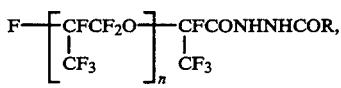

wherein R represents one member selected from the group consisting of a hydrogen atom, an alkyl group and an aromatic group;

V: a diacylhydrazine having an average molecular weight of 500 to 20,000 and represented by the formula 31

and

VI: a diacylhydrazine having a molecular weight of 500 to 200,000 and represented by the formula 32

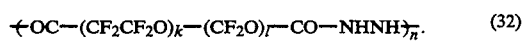

2. A diacylhydrazine according to claim 1, having an average molecular weight of 500 to 20,000 and represented by the formula 27;

3. A diacylhydrazine according to claim 1, having an average molecular weight of 500 to 20,000 and represented by the formula 28;

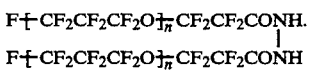

4. A diacylhydrazine according to claim 1, having an average molecular weight of 500 to 20,000 and represented by the formula 29;

5. A diacylhydrazine according to claim 1, having an average molecular weight of 500 to 20,000 and represented by the formula 30;

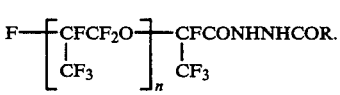

6. A diacylhydrazine according to claim 1, having an average molecular weight of 500 to 20,000 and represented by the formula 31;

7. A diacylhydrazine according to claim 1, having an average molecular weight of 500 to 200,000 and represented by the formula 32;

* * * * *